(12) United States Patent
Walker (10) Patent No.: US 9,250,207 B2
(45) Date of Patent: *Feb. 2, 2016

(54) CONTROLLED TRANSLOCATION OF MACROMOLECULES EMPLOYING A FUNNEL NANOPORE STRUCTURE AND A GEL

(71) Applicant: International Business Machines Corporation, Armonk, NY (US)

(72) Inventor: George F. Walker, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 202 days.

This patent is subject to a terminal disclaimer.

(21) Appl. No.: 14/022,718

(22) Filed: Sep. 10, 2013

(65) Prior Publication Data

US 2014/0299473 A1 Oct. 9, 2014

Related U.S. Application Data

(63) Continuation of application No. 13/856,550, filed on Apr. 4, 2013.

(51) Int. Cl.
G01N 27/447 (2006.01)
(52) U.S. Cl.
CPC .... *G01N 27/44704* (2013.01); *G01N 27/44747* (2013.01)
(58) Field of Classification Search
CPC .................................................. G01N 27/447
See application file for complete search history.

(56) References Cited

U.S. PATENT DOCUMENTS

| 7,914,656 | B2 | 3/2011 | Bukshpan et al. |
| 2003/0077642 | A1* | 4/2003 | Fritsch et al. ..................... 435/6 |
| 2006/0231419 | A1* | 10/2006 | Barth et al. .................. 205/775 |
| 2008/0121534 | A1* | 5/2008 | White et al. ............... 205/787.5 |
| 2010/0035260 | A1* | 2/2010 | Olasagasti et al. ................ 435/6 |
| 2010/0327847 | A1 | 12/2010 | Leiber et al. |

(Continued)

FOREIGN PATENT DOCUMENTS

WO 2013/016486 A1 1/2013

OTHER PUBLICATIONS

Venkatesan et al. (ACS Nano. Jan. 24, 2012; 6(1): 441-450).*

(Continued)

*Primary Examiner* — Jennifer Dieterle
(74) *Attorney, Agent, or Firm* — Scully, Scott, Murphy & Presser, P.C.; Louis J. Percello, Esq.

(57) ABSTRACT

A system of controlled translocation of macromolecules by gel electrophesis employs a funnel nanopore structure. A graphene portion is attached to a porous material layer including funnel-shaped pores such that the graphene portion blocks the side of the porous material layer having openings for smaller pores. A pair of electrical contacts is formed on the graphene portion. A dielectric material layer may be deposited to hold the graphene portion in place. A nanoscale hole is formed through the dielectric material layer and the graphene portion to provide a smallest opening in a funnel nanopore structure. The funnel nanopore structure is placed within a capsule configured for gel electrophoresis. A linear chain of molecules can pass through a funnel-shaped pore and the nanoscale hole during the gel electrophoresis. A graphene nanopore detector allows measurement of blockage current for sufficient resolution of base pairs in DNA's.

7 Claims, 7 Drawing Sheets

(56) References Cited

U.S. PATENT DOCUMENTS

| 2011/0108422 | A1* | 5/2011 | Heller et al. ............... 204/547 |
| 2012/0037919 | A1 | 2/2012 | Xu et al. |
| 2012/0040343 | A1 | 2/2012 | Timp et al. |
| 2012/0208705 | A1 | 8/2012 | Steemers et al. |
| 2012/0234679 | A1 | 9/2012 | Garaj et al. |
| 2012/0241371 | A1 | 9/2012 | Revanur et al. |
| 2012/0255899 | A1 | 10/2012 | Choi et al. |
| 2012/0322055 | A1* | 12/2012 | Royyuru ................. 435/6.1 |
| 2015/0069329 | A1* | 3/2015 | Jeon et al. ................. 257/29 |

OTHER PUBLICATIONS

Valota et al. (ACSNANO vol. 5, No. 11, 8809-8815, 2011).*

International Preliminary Report on Patentability together with the Written Opinion dated Nov. 5, 2014, received in related International Application No. PCT/US2014/030991.

Garaj et al, "Graphene as a subnanometre trans-electrode membrane" Nature (Sep. 9, 2010) pp. 190-193, vol. 467, No. 7312.

Bayley, "Nanotechnology: holes with an edge" Nature (Sep. 9, 2010) pp. 164-165, vol. 467, No. 7312.

Heng et al., "The electromechanics of DNA in a synthetic nanopore" Biophysical Journal (Feb. 2006) pp. 1098-1106, vol. 90, No. 3.

Cherf et al., "Automated forward and reverse ratcheting of DNA in a nanopore at 5-Å precision" Nature Biotechnology (Feb. 14, 2012) pp. 344-348, vol. 30, No. 4.

Postma, "Rapid Sequencing of Individual DNA Molecules in Graphene Nanogaps" Nano Lett. (Jan. 4, 2010) pp. 420-425, vol. 10, No. 2.

PCT Invitation to Pay Additional Fees and, Where Applicable, Protest Fee, form PCT/ISA/206, dated Aug. 5, 2014 from related International PCT Application No. PCT/US2014/030991.

Liu et al., "Mechanisms of water infiltration into conical hydrophobic nanopores", First published as an Advance Article on the web Jun. 12, 2009, (Phys. Chem. Chem. Phys., 2009, 11, 6520-6524) document was downloaded from http://tees.openrepository.com/tees/handle/10149/315329.

Office Action dated Jun. 8, 2015 received in a related U.S. Appl. No. 13/856,550.

* cited by examiner

CONTROLLED TRANSLOCATION OF MACROMOLECULES EMPLOYING A FUNNEL NANOPORE STRUCTURE AND A GEL

CROSS REFERENCE TO RELATED APPLICATION

This application is a continuation of U.S. patent application Ser. No. 13/856,550, filed Apr. 4, 2013 the entire content and disclosure of which is incorporated herein by reference.

BACKGROUND

The present disclosure generally relates to a method of translocating macromolecules, and particularly to a method of translocating macromolecules employing a funnel nanopore structure and a gel, and structures and apparatuses for affecting the same.

Many macromolecules including deoxyribonucleic acid (DNA) have a shape of a linear chain and are conducive to sequencing. In order to provide sequencing of a linear chain of a macromolecule, however, the macromolecule must be allowed to move along the direction of the lengthwise chain. Thus, a method of geometrically orientating a linear chain of a macromolecule with respect to a measurement device is desired.

SUMMARY

A system of controlled translocation of macromolecules by gel electrophoresis employs a funnel nanopore structure. A graphene portion is attached to a porous material layer including funnel-shaped pores such that the graphene portion blocks the side of the porous material layer having openings for smaller pores relative to pores on the opposite side. A pair of electrical contacts is formed on the graphene portion. A dielectric material layer may be deposited to hold the graphene portion in place. A nanoscale hole is formed through the dielectric material layer and the graphene portion to provide a smallest opening in a funnel nanopore structure. The funnel nanopore structure is placed within a capsule configured for gel electrophoresis. A linear chain of molecules can pass through a funnel-shaped pore and the nanoscale hole during the gel electrophoresis, and a change in a blockage current in a circuit including the graphene portion can be measured as the linear chain passes through the opening to collect information on the structure of the macromolecule. A graphene nanopore detector allows measurement of blockage current for sufficient resolution of base pairs in DNA's.

According to an aspect of the present disclosure, a gel electrophoresis apparatus is provided. The gel electrophoresis apparatus includes an enclosure divided into a first chamber and a second chamber by a divider plate. The divider plate includes a porous material layer including funnel-shaped pores between a first side surface and a second side surface, wherein each of the funnel-shaped pores has a smaller opening at the first side surface than at the second side surface, and a graphene portion contacting the first side surface, wherein a nanoscale hole extends through the graphene portion and to one of the funnel-shaped pores. A first electrode is provided in the first chamber, and a second electrode is provided in the second chamber. Further, a circuitry configured to provide a voltage across the first electrode and the second electrode is also provided.

According to another aspect of the present disclosure, a structure is provided, which includes a porous material layer including funnel-shaped pores between a first side surface and a second side surface, wherein each of the funnel-shaped pores has a smaller opening at the first side surface than at the second side surface. The structure further includes a graphene portion contacting the first side surface, wherein a nanoscale hole extends through the graphene portion and to one of the funnel-shaped pores.

According to yet another aspect of the present disclosure, a method of operating an apparatus is provided. An apparatus is provided, which includes an enclosure divided into a first chamber and a second chamber by a divider plate, the divider plate including a porous material layer including funnel-shaped pores between a first side surface and a second side surface. The first side surface is a peripheral surface of the first chamber and the second side surface is a peripheral surface of the second chamber, and each of the funnel-shaped pores has a smaller opening at the first side surface than at the second side surface. The enclosure is filled with a sol. The sol is converted into a gel. Macromolecules including a linear chain are inserted into the first chamber. The macromolecules are induced to pass through the divider plate by performing gel electrophoresis across the first chamber and the second chamber.

DETAILED DESCRIPTION

As stated above, the present disclosure relates to a method of translocating macromolecules, and particularly to a method of translocating macromolecules employing a funnel nanopore structure and a gel, and structures and apparatuses for effecting the same. Aspects of the present disclosure are now described in detail with accompanying figures. It is noted that like reference numerals refer to like elements across different embodiments. The drawings are not necessarily drawn to scale. As used herein, ordinals such as "first," "second," and "third," etc. are employed to distinguish similar elements, and a same element may be labeled with different ordinals across the specification and the claims.

Figure 1A:
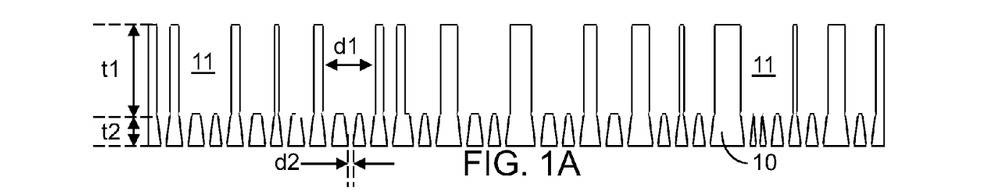
FIG. 1A is a vertical cross-sectional view of a first exemplary structure including a porous material layer including funnel-shaped pores according to an embodiment of the present disclosure.
Figure 1B:
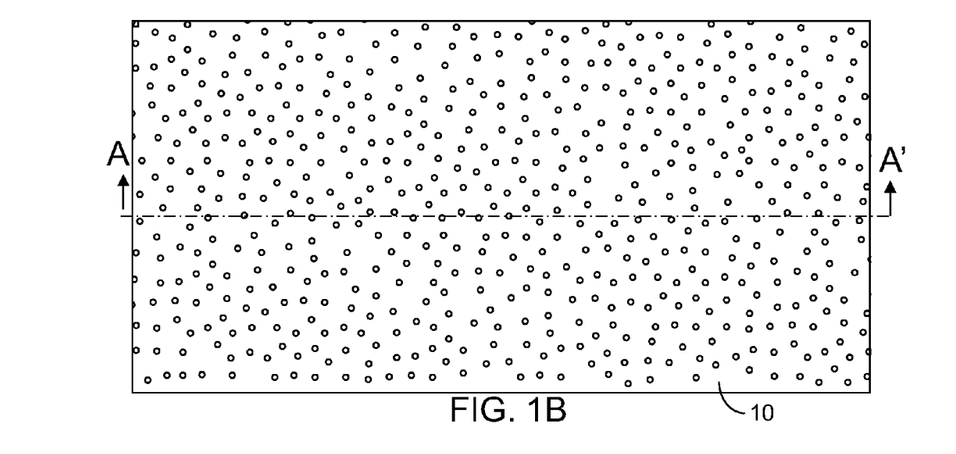
FIG. 1B is a bottom side view of the first exemplary structure of FIG. 1A. The A-A' plane refers to the plane of the vertical cross-section of FIG. 1A.
Figure 1C:
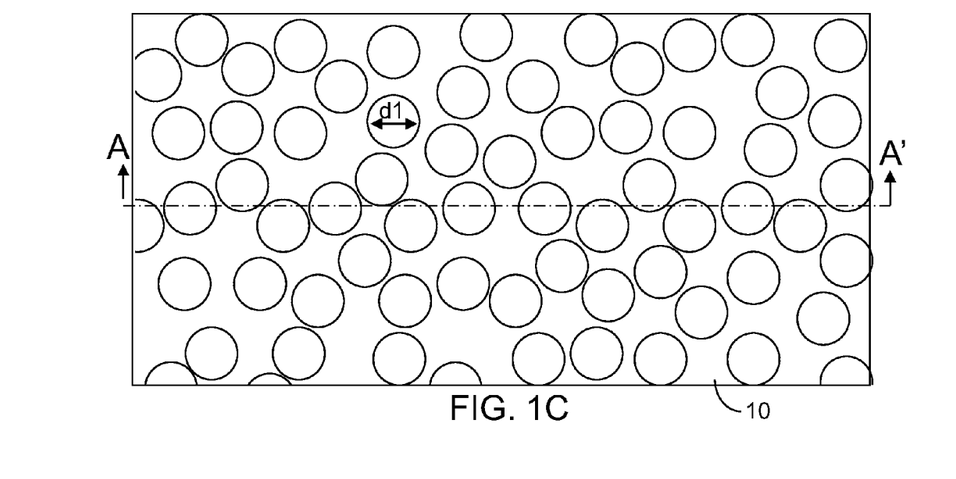
FIG. 1C is a top side view of the first exemplary structure of FIG. 1A. The A-A' plane refers to the plane of the vertical cross-section of FIG. 1A.

Referring to FIGS. 1A, 1B, and 1C, a first exemplary structure according to an embodiment of the present disclosure includes a porous material layer 10 including funnel-shaped pores 11. As used herein, a "funnel-shaped pore" refers to a pore extending to at least one opening in a surface of a matrix structure in which the pore is embedded such that a cross-sectional area of an end portion of the pore decreases toward each of the at least one opening. Each funnel-shaped pore 11 in the porous material layer 10 includes at least one tapered portion in which the cross-sectional area decreases with distance from a geometrical center of the funnel-shaped pore 11. As used herein, a geometrical center of a pore refers to a point corresponding to the mathematical average of all Cartesian coordinates of the pore. Each funnel-shaped pore 11 extends from the front side (the top side in FIG. 1A and shown in FIG. 1C) of the porous material layer 10 to the back side (the bottom side in FIG. 1A and shown in FIG. 1B) of the porous material layer 10. The back surface is herein referred to as a first side surface (i.e., a surface that is on a first side), and the front surface is herein referred to as a second side surface (i.e., a surface that is on a second side). Each funnel-shaped pore 11 can extend between the first side surface and the second side surface. Each funnel-shaped pore 11 includes one opening on the front side, and at least one opening on the back side. A funnel-shaped pore 11 can include a plurality of openings on the back side, i.e., can be multi-pronged pores such that multiple tapered portions are adjoined to a main cavity having a greater lateral dimension. Each of the funnel-shaped pores 11 can have a smaller opening at the first side surface than at the second side surface.

The porous material layer 10 includes a dielectric material. In one embodiment, the porous material layer 10 can consist essentially of a dielectric material. In one embodiment, the porous material layer 10 can consist essentially of a dielectric ceramic material. In one embodiment, the porous material layer 10 can consist essentially of a dielectric metal oxide. In one embodiment, the porous material layer 10 can include aluminum oxide ($Al_2O_3$).

In one embodiment, the porous material layer 10 can consist essentially of aluminum oxide. In one embodiment, each funnel-shaped pore 11 may include a substantially uniform pore portion in which a cross-sectional area does not change substantially (i.e., by more than 20%), and at least one tapered portion in which the cross-sectional area decreases with distance from a geometrical center of the funnel-shaped pore 11. In one embodiment, the average of lateral dimensions of the substantially uniform pore portion is herein referred to as a first lateral dimension d1. The first lateral dimension d1 may be the average of diameters or major axes of the horizontal cross-sectional areas (i.e., a cross-sectional area within a plane that is parallel to the first side surface and the second side surface) of the substantially uniform pore portions if the horizontal cross-sectional areas have circular or elliptical shapes. In one embodiment, the first lateral dimension d1 may be in a range from 50 nm to 800 nm at the second side surface (as seen in FIG. 1C) and throughout the substantially uniform pore portion, although lesser and greater dimensions can also be employed. In one embodiment, the first lateral dimension d1 may greater than 100 nm. In another embodiment, the first lateral dimension d1 may be greater than 200 nm. In one embodiment, the first lateral dimension d1 may be less than 200 nm. In another embodiment, the first lateral dimension d1 may be less than 100 nm.

The average of the lateral dimensions of openings of the funnel-shaped pore 11 at the first side surface (as seen in FIG. 1B) is herein referred to as a second lateral dimension d2. The second lateral dimension d2 may be a diameter or a major axis of an opening of a funnel-shaped pore 11 on the first side surface. In one embodiment, the second lateral dimension d2 may be in a range from 4 nm to 50 nm at the first side surface, although lesser and greater dimensions can also be employed. In one embodiment, the second lateral dimension d2 may greater than 10 nm. In another embodiment, the second lateral dimension d2 may be greater than 20 nm. In one embodiment, the second lateral dimension d2 may be less than 20 nm. In another embodiment, the second lateral dimension d2 may be less than 10 nm.

The thickness of the substantially uniform pore portions, i.e., the dimension of the substantially uniform pore portions as measured along a direction perpendicular to the first side surface and the second side surface, is herein referred to as a first thickness t1. The first thickness t1 may be in a range from 20 microns to 500 microns, although lesser and greater thicknesses can also be employed. In one embodiment, the first thickness t1 can be greater than 30 microns. In another embodiment, the first thickness t1 can be greater than 40 microns. In one embodiment, the first thickness t1 can be less than 200 microns. In another embodiment, the first thickness t2 can be less than 100 microns.

The thickness of the tapered portions of the funnel-shaped pores 11, i.e., the dimension of the tapered portions as measured along a direction perpendicular to the first side surface and the second side surface, is herein referred to as a second thickness t2. The second thickness t2 may be in a range from 20 nm to 100 nm, although lesser and greater thicknesses can also be employed.

The lateral dimension of the porous material layer 10, i.e., the extent of the porous material layer 10 within the plane of the first side surface or within the plane of the second side surface, can be in a range from 0.5 cm to 10 cm, although lesser and greater dimensions can also be employed.

In one embodiment, a commercially available product may be employed as the porous material layer 10. For example, Whatman® Anotop® 10 syringe filters made of aluminum oxide and commercially available from Whatman GmbH may be employed as the porous material layer 10 for the purpose of the present disclosure. The total thickness (i.e., t1+t2) of the porous material layer 10 as provided may be about 53 microns, and the first lateral dimension d1 may be about 200 nm, and the second lateral dimension d2 may be about 25 nm.

In one embodiment, the porous material layer 10 may be coated with a dielectric material layer (not shown) to reduce the size of the second lateral dimension. The dielectric material layer includes a dielectric material that may be conformally deposited by atomic layer deposition (ALD) or chemical vapor deposition (CVD). The dielectric material can be a dielectric metal oxide such as aluminum oxide, titanium oxide, hafnium oxide, zirconium oxide, or can be a dielectric semiconductor oxide such as silicon oxide, or can be a dielectric metal nitride, or can be a dielectric semiconductor nitride such as silicon nitride. The thickness of the deposited dielectric material layer is selected such that the openings at the first side surface of the funnel-shaped pores are not sealed by the dielectric material layer. The second lateral dimension d2 after deposition of the dielectric material layer can be in a range from 4 nm to 20 nm, although lesser and greater second lateral dimensions d2 can also be employed.

Figure 2A:
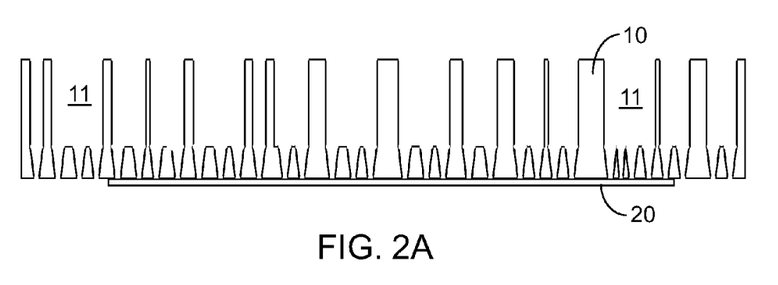
FIG. 2A is a vertical cross-sectional view of the first exemplary structure after disposing a graphene portion on a bottom surface of the porous material layer according to an embodiment of the present disclosure.
Figure 2B:
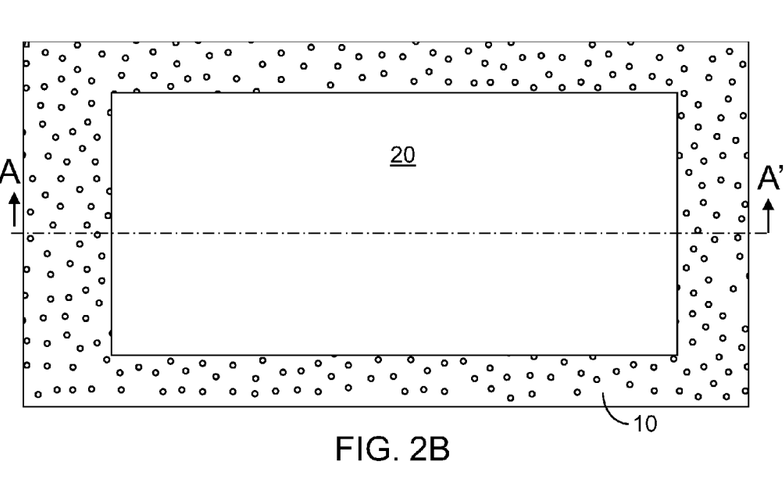
FIG. 2B is a bottom side view of the first exemplary structure of FIG. 2A. The A-A' plane refers to the plane of the vertical cross-section of FIG. 2A.

Referring to FIGS. 2A and 2B, at least one graphene portion 20 is disposed on the first side surface of the porous material layer 10. Each graphene portion 20 is a piece of a graphene sheet that is patterned into a suitable shape, for example, by cutting. A graphene sheet can be provided by any method known in the art, and is patterned, for example, by cutting with a sharp instrument such as a pair of scissors or another cutting device, into one or more of the graphene portions 20. Each graphene portion 20 can have a polygonal shape (such as a rectangular shape), or a curvilinear shape in which at least one edge has a curved profile. The lateral dimensions of a graphene portion 20 can be in a range from 100 microns to 3 mm, although lesser and greater dimensions can also be employed. In an illustrative example, each graphene portion 20 can have a rectangular shape such that the length of the rectangle can be 1 mm and the width of the rectangle can be 100 microns. The at least one graphene portion 20 may be disposed on the first side surface of the porous material layer 10 in air, in vacuum, or in a solution from which a combination of the at least one graphene portion 20 and the porous material layer 10 can be scooped. In one embodiment, a single graphene portion 20 may be disposed on the porous material layer 10. In another embodiment, a plurality of graphene portions 20 may be disposed on the porous material layer 10.

Figure 3A:
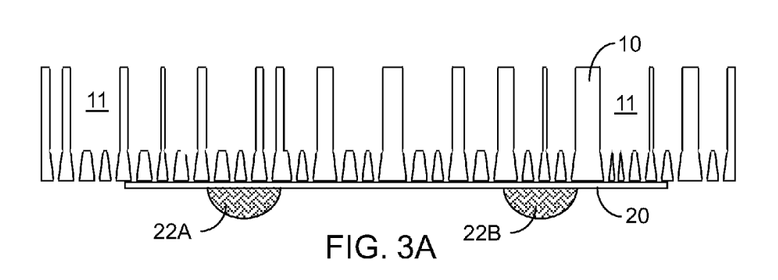
FIG. 3A is a vertical cross-sectional view of the first exemplary structure after formation of contact structures on the graphene portion according to an embodiment of the present disclosure.
Figure 3B:
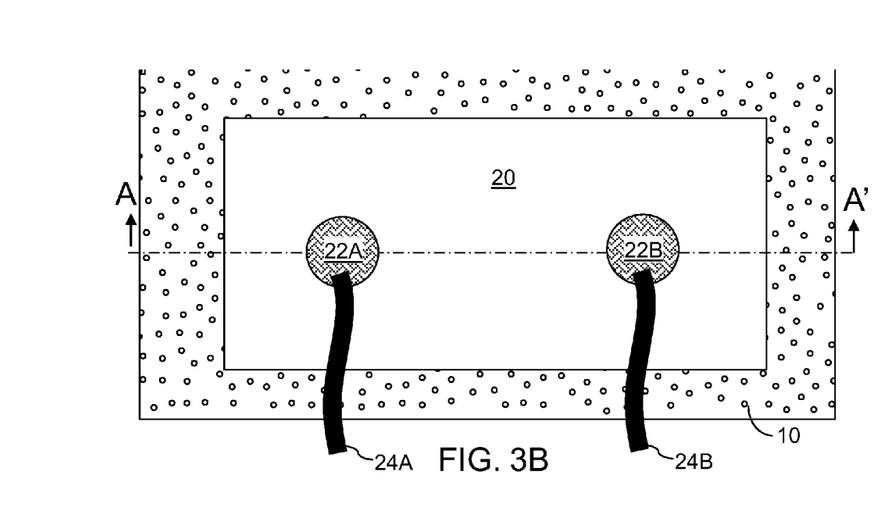
FIG. 3B is a bottom side view of the first exemplary structure of FIG. 3A. The A-A' plane refers to the plane of the vertical cross-section of FIG. 3A.

Referring to FIGS. 3A and 3B, a pair of contact structures (22A, 22B) is formed on each graphene portion 20. The pair of contact structures (22A, 22B) includes a first contact structure 22A and a second contact structure 22B that are laterally spaced from each other. In one embodiment, the first contact structure 22A and the second contact structure 22B can be formed on opposite sides of the graphene portion 20 with respect to a geometrical center of the graphene portion 20. Thus, the pair of contact structures (22A, 22B) is in physical contact with two regions of the graphene portion 20.

The pair of contact structures (22A, 22B) includes a material that forms a metallurgical contact with the graphene portion 20. Non-limiting examples of metallic materials that can be employed for the pair of contact structures (22A, 22B) include gold, palladium, tungsten, titanium, alloys thereof, and combinations thereof. The lateral dimensions of each contact structure (22A, 22B) can be in a range from 1 micron to 10 microns, although lesser and greater dimensions can also be employed. The pair of contact structures (22A, 22B) may be formed, for example, by a masked evaporation process, a masked sputtering process, or any other known method for forming metallurgical contacts on a graphene sheet. A pair of conductive lead wires (24A, 24B) is attached to the pair of contact structures (22A, 22B). A first conductive lead wire 24A can be attached to the first contact structure 22A, and a second conductive lead wire 24B can be attached to the second contact structure 22B. The first conductive lead wire 24A and the second conductive lead wire 24B can be metal wires, and can be attached to the pair of contact structures (22A, 22B), for example, by soldering or any other method of attaching a metal wire to a metallic material. The pair of contact structures (22A, 22B) and the pair of conductive lead wires (24A, 24B) can be subsequently employed to measure the blockage current of the graphene portion 20 as disturbed by a combination of a nanoscale hole (not shown) to be subsequently formed and atoms of a linear chain of a macromolecule (not shown) to pass through the hole during a measurement step.

Figure 4A:
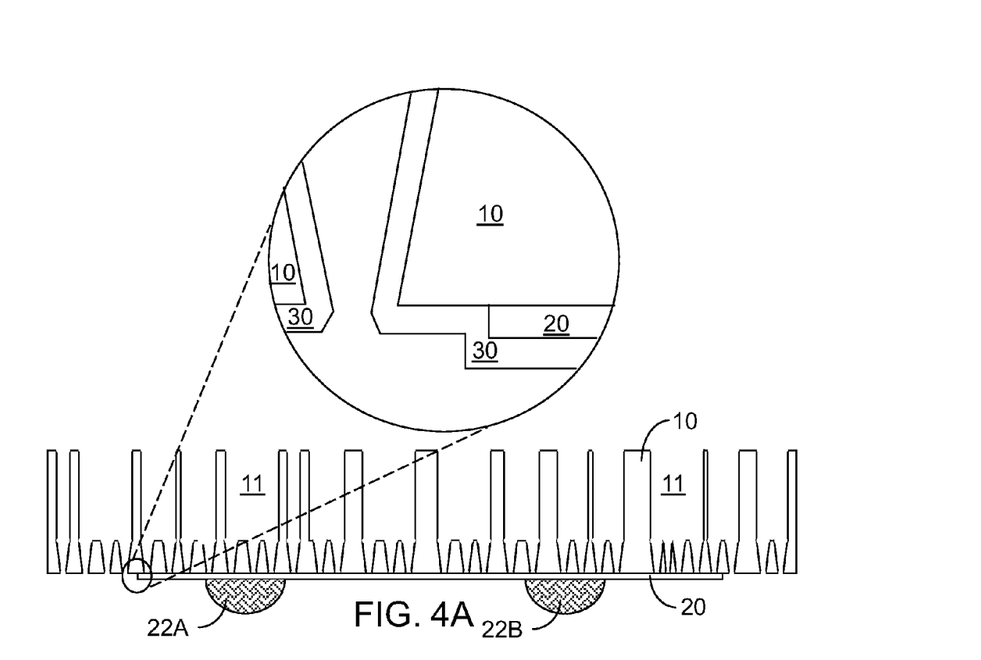
FIG. 4A is a vertical cross-sectional view of the first exemplary structure after formation of a dielectric material layer according to an embodiment of the present disclosure.
Figure 4B:
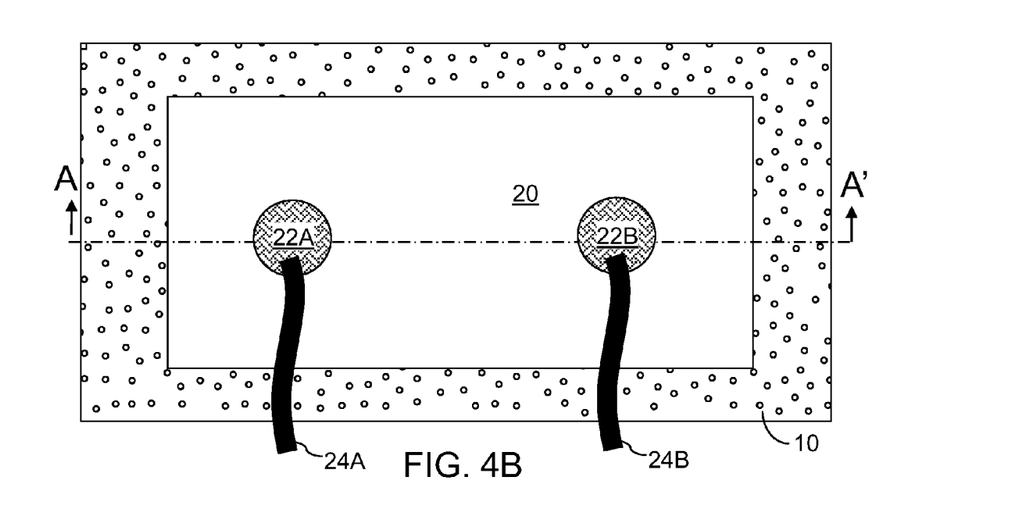
FIG. 4B is a bottom side view of the first exemplary structure of FIG. 4A. The A-A' plane refers to the plane of the vertical cross-section of FIG. 4A.

Referring to FIGS. 4A and 4B, a dielectric material layer 30 is deposited on the bottom side of the first exemplary structure. Specifically, the dielectric material layer 30 can be deposited on the physically exposed surfaces of the at least one graphene portion 20, the contact structures (22A, 22B), and the physically exposed portions of the first side surface of the porous material layer 10. In one embodiment, an insulation coating may be formed on physically exposed surfaces of the conductive lead wires (24A, 24B). If a conformal deposition method such as atomic layer deposition (ALD) or chemical vapor deposition (CVD) is employed, the dielectric material layer 30 can be formed on the inner surfaces of the funnel-shaped pores 11. Thus, a coating of the dielectric material layer 30 is formed on the outer surface of each graphene portion 20 and portions of the first side surface that are not in contact with the graphene portion 20.

All physically exposed surfaces of each graphene portion 20 can be coated with the dielectric material layer 30. Thus, all surfaces of each graphene portion 20 not in contact with the porous material layer 10 are coated with the dielectric material layer 20. The dielectric material layer 30 can include a dielectric metal oxide material such as aluminum oxide, titanium oxide, hafnium oxide, zirconium oxide, lanthanum oxide, or combinations or stacks thereof, and/or can include silicon nitride. The thickness of the dielectric material layer 30 can be in a range from 1 nm to 4 nm, although lesser and greater thicknesses can also be employed. The dielectric material layer 30, in combination with the porous material layer 10, seals each graphene portion 20, and protects each graphene portion 20 from contaminants during subsequent use of the first exemplary structure as a divider plate for a gel electrophoresis apparatus or for other applications. As used herein, "gel electropheresis" refers to electrophoresis in a gel medium. Further, a coating of the dielectric material layer 30 on the contact structures (22A, 22B) and the conductive lead wires (24A, 24B) provides electrical insulation for the contact structures (22A, 22B) and the conductive lead wires (24A, 24B). The dielectric material layer 30 can be formed, for example, by atomic layer deposition (ALD) or chemical vapor deposition (CVD).

Figure 5A:
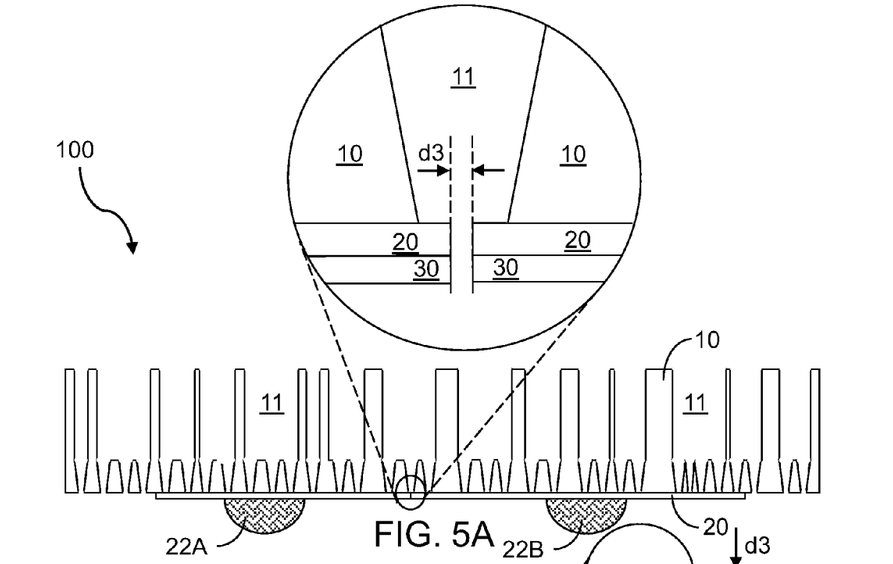
FIG. 5A is a vertical cross-sectional view of the first exemplary structure after formation of a nanoscale hole through the dielectric material layer and the graphene portion according to an embodiment of the present disclosure.
Figure 5B:
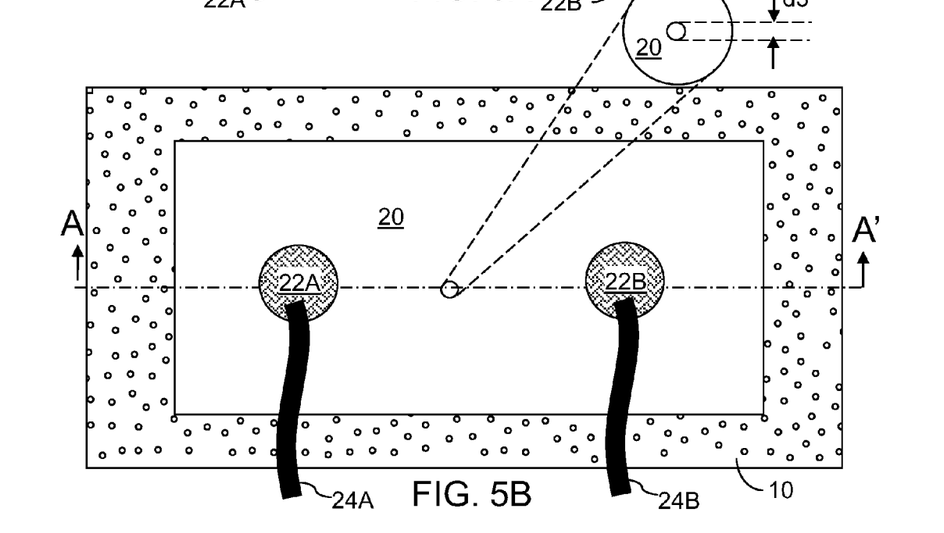
FIG. 5B is a bottom side view of the first exemplary structure of FIG. 5A. The A-A' plane refers to the plane of the vertical cross-section of FIG. 5A.

Referring to FIGS. 5A and 5B, for each graphene portion 20, a nanoscale hole is formed through the dielectric material layer 30 and the graphene portion 20. A single nanoscale hole can be formed per each graphene portion 20. As used herein, a nanoscale hole refers to a hole having a lateral dimension in a range from 1 nm to 10 nm. This lateral dimension is herein referred to as third lateral dimension d3. In one embodiment, the nanoscale hole can have a substantially circular opening area. In one embodiment, the nanoscale hole may have a diameter in a range from 1 nm to 10 nm. In one embodiment, the diameter of the nanoscale hole can be greater than 1.3 nm.

In another embodiment, the diameter of the nanoscale hole can be greater than 1.7 nm. In one embodiment, the diameter of the nanoscale hole can be less than 5 nm. In another embodiment, the diameter of the nanoscale hole can be less than 3 nm.

The nanoscale hole may be formed, for example, by an electron beam that ablates the materials of the dielectric material layer 30 and the graphene portion 20. For example, the electron beam can have an energy in a range from 200 keV to 400 keV, although lesser and greater beam energies can also be employed. The nanoscale hole extends through the dielectric material layer 30 and through the graphene portion 20. The nanoscale hole can be formed between the pair of contact structures (22A, 22B). Thus, the distance between the pair of contact structures (22A, 22B) is greater than the distance between the nanoscale hole and any of the pair of contact structures (22A, 22B). In one embodiment, the location of the nanoscale hole can be selected such that the nanoscale hole is formed approximately at a geometrical center of the pair of contact structures (22A, 22B) so as to maximize disturbance in the ballistic transport of electrons between the pair of contact structures (22A, 22B) in the punctured graphene portion 20. The assembly of the porous material layer 10, the at least one graphene portion 20 including a nanoscale hole, the contact structures (22A, 22B), the conductive lead wires (24A, 24B), and the dielectric material layer 30 is herein collectively referred to as a plate structure 100, which is subsequently employed as a divider plate between two chambers in a gel electrophoresis apparatus.

Figure 6:
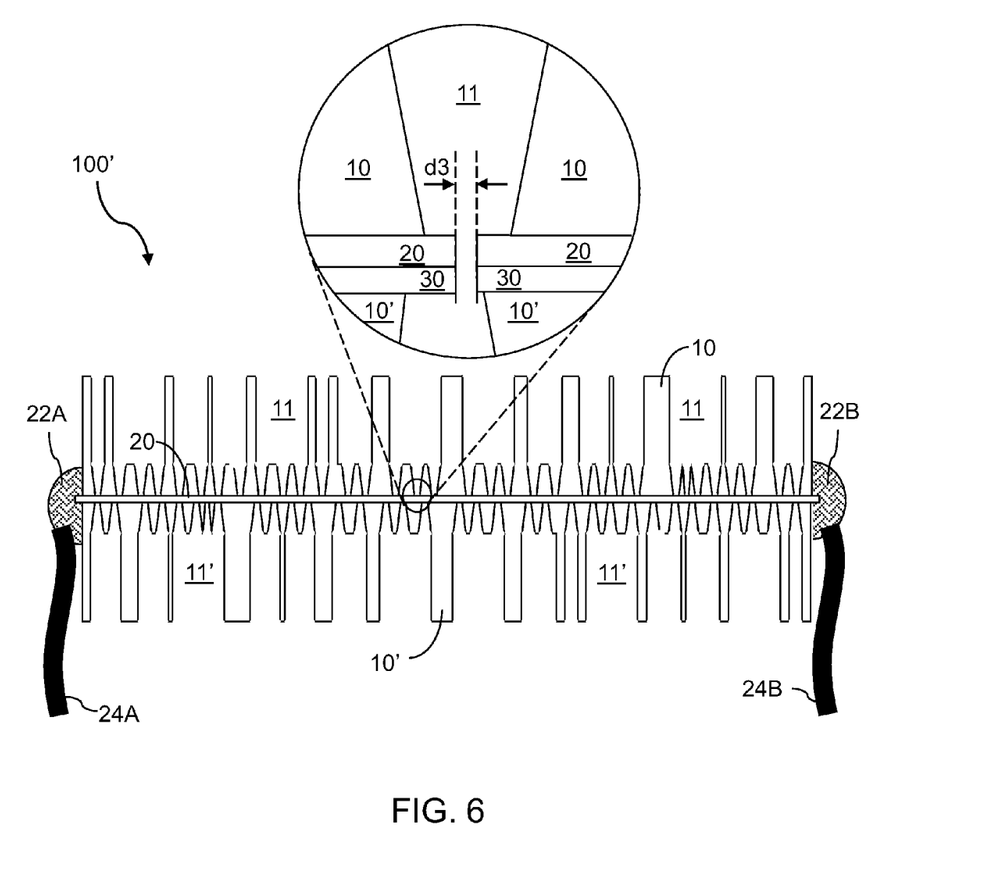
FIG. 6 is a vertical cross-sectional view of a second exemplary structure after attaching another porous material layer to the graphene portion or to the dielectric material layer and formation of contact structures on the graphene portion according to an embodiment of the present disclosure.

Referring to FIG. 6, a second exemplary structure can be derived from the first exemplary structure by attaching another porous material layer (which is herein referred to as a second porous material layer 10') to the at least one graphene portion 20, or to the dielectric material layer 30. The second porous material layer 10' can have any of the geometrical features that the porous material layer 10 described above can have. Further, the second porous material layer 10' can have any composition that the porous material layer 10 described above can have. The composition of the porous material layer 10 and the second porous material layer 10' may be the same, or different. Particularly, the second porous material layer 10' includes additional funnel-shaped pores 11', which can have the any or all of the geometrical features as the funnel-shaped pores 11 described above.

The dielectric material layer 30 may, or may not, be employed in the second exemplary structure. An assembly of the porous material layer 10, the at least one graphene portion 20 including a nanoscale hole, and the optional dielectric material layer 30 is formed by performing the processing steps of FIGS. 1A-1C, 2A-2B, and 5A-5B without performing the processing steps of FIGS. 3A-3B. The processing steps of FIGS. 4A-4B may, or may not, be performed. Subsequently, the second porous material layer 10' is disposed directly on the at least one graphene portion 20 or indirectly on the at least one graphene portion 20 through the dielectric material layer 30.

The second porous material layer 10' includes additional funnel-shaped pores 11' between a surface that contacts the at least one graphene portion 20 or the dielectric material layer 30 (which is herein referred to as a proximal side surface) and a surface that does not contact the at least one graphene portion 20 or the dielectric material layer 30 (which is herein referred to as a distal side surface). The second porous material layer 10' is disposed such that tapered portions of the additional funnel-shaped pores 11' are closer to the at least one graphene portion 20 than substantially uniform pore portions of the additional funnel-shaped pores 11'. The distal side surface is more distal from the at least one graphene portion 30 than the proximal side surface. The proximal surface and the distal surface of the second porous material layer 10' can be parallel to the first side surface and the second side surface of the porous material layer 10. Thus, each of the additional funnel-shaped pores 11' can have a smaller opening at the proximal side surface than at the distal side surface.

The second porous material layer 10' can be affixed to the first porous material layer 10 by any mechanical means including, but not limited to, at least one clip, an adhesive, at least one screw, at least one bolt and at least one nut, external mechanical structures configured to press against the second porous material layer 10' and the porous material layer 10, or a combination thereof.

Each graphene portion 20 can be sized so that end regions of the graphene portion 20 protrude out of the peripheries of the porous material layer 10 and/or peripheries of the second porous material layer 10'. A pair of contact structures (22A, 22B) can subsequently be formed on each graphene portion 20. The pair of contact structures (22A, 22B) includes a first contact structure 22A and a second contact structure 22B that are laterally spaced from each other. In one embodiment, the first contact structure 22A and the second contact structure 22B can be formed on opposite sides of the graphene portion 20 with respect to a geometrical center of the graphene portion 20. Thus, the pair of contact structures (22A, 22B) is in physical contact with two regions of the graphene portion 20. The pair of contact structures (22A, 22B) may be formed on peripheral surfaces of the assembly of the porous material layer 10, the second porous material layer 10', the at least one graphene portion 20 including a nanoscale hole, the contact structures (22A, 22B), the conductive lead wires (24A, 24B), and the optional dielectric material layer 30 is herein collectively referred to as a plate structure 100', which is subsequently employed as a divider plate between two enclosures in a gel electrophoresis apparatus.

The pair of contact structures (22A, 22B) includes a material that forms a metallurgical contact with the graphene portion 20. Non-limiting examples of metallic materials that can be employed for the pair of contact structures (22A, 22B) include gold, silver, titanium, palladium, tungsten, alloys thereof, and combinations thereof. The lateral dimensions of each contact structure (22A, 22B) can be in a range from 1 micron to 10 microns, although lesser and greater dimensions can also be employed. The pair of contact structures (22A, 22B) may be formed, for example, by a masked evaporation process, a masked sputtering process, or any other known method for forming metallurgical contacts on a graphene sheet. A pair of conductive lead wires (24A, 24B) is attached to the pair of contact structures (22A, 22B). A first conductive lead wire 24A can be attached to the first contact structure 22A, and a second conductive lead wire 24B can be attached to the second contact structure 22B. The first conductive lead wire 24A and the second conductive lead wire 24B can be metal wires, and can be attached to the pair of contact structures (22A, 22B), for example, by soldering or any other method of attaching a metal wire to a metallic material. The pair of contact structures (22A, 22B) and the pair of conductive lead wires (24A, 24B) can be subsequently employed to measure the blockage current of the graphene portion 20 as disturbed by a combination of a nanoscale hole (not shown) to be subsequently formed and atoms of a linear chain of a macromolecule (not shown) to pass through the hole during a measurement step. As used herein, a "blockage current" refers to a variation in electrical current due to passage of an object through a hole in a conductive medium such as a graphene portion.

Figure 7:
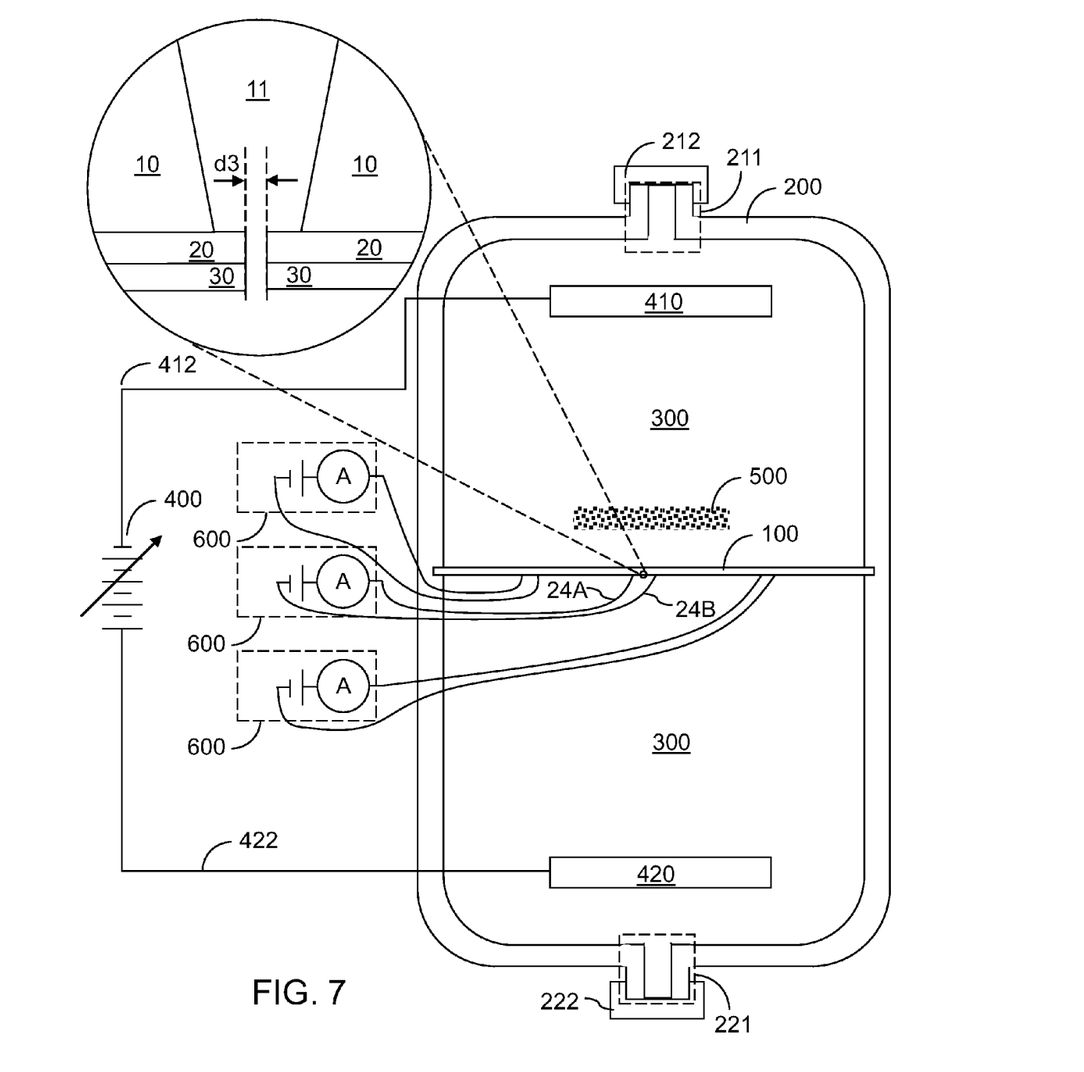
FIG. 7 is a schematic view illustrating an exemplary gel electrophoresis apparatus employing the first exemplary structure or the second exemplary structure as a divider plate according to an embodiment of the present disclosure.

FIG. 7 illustrates an exemplary gel electrophoresis apparatus employing the first exemplary structure or the second exemplary structure as a divider plate. Specifically, the plate structure (100 or 100') described above can be employed as the divider plate between two chambers in an enclosure configured for gel electrophoresis. The enclosure includes an enclosure 200, which provides a contiguous sealed space in conjunction with a first enclosure opening cap 212 that seals a first enclosure opening 211 and a second enclosure opening cap 222 that seals a second enclosure opening 221. The enclosure is configured to hold the plate structure (100 or 100') such that the plate structure (100 or 100') functions as a divider plate that divides the enclosure into a first chamber (e.g., the chamber above the plate structure (100 or 100')) and a second chamber (100 or 100'). In one embodiment, the plate structure (100 or 100') can be oriented such that the second side surface of the porous material layer 10 faces the first enclosure opening 211 that can be sealed by the first enclosure opening cap 212. The enclosure is a fluidic enclosure to be filled with a gel after a sol/gel transition, and as such, is liquid-tight when sealed.

The enclosure can be in multiple pieces (such as a container and a line) or in a clam shell configuration so that the two chambers of the enclosure can be subsequently accessed for insertion of a first electrode 410 into the first chamber and for insertion of a second electrode 420 into the second chamber. Alternatively, the first electrode 410 can be loaded into the first chamber and the second electrode 420 can be loaded into the second chamber before, during, or after installation of the plate structure (100 or 100') onto the walls of the enclosure 200. The first electrode 410 and/or the second electrode 420 can be affixed to the walls of the enclosure 200. The enclosure may be sealed after installation of the plate structure (100 or 100'), the first electrode 410, and the second electrode 420, while maintaining the ability to remove the first enclosure opening cap 212 and the second enclosure opening cap 222.

Conductive lead wires (24A, 24B), which are electrically insulated from the environment by an insulator layer (not shown) or by the dielectric material layer 30 (See FIGS. 4A and 4B), are routed to the outside of the enclosure through enclosure walls or through a sealed gap (e.g., between a container and a lid of the enclosure or between a sealing surface in a clamshell configuration) to current detectors 600 configured to measure the blockage current of each graphene portion 20 (See FIGS. 5A and 5B) as perturbed by a nanoscale hole in each graphene portion 20 and a linear chain of a macromolecule to pass therethrough. Each current detector 600 can be configured to provide a predetermined voltage and measure the blockage current through an electrical circuit including a graphene portion 20, or can be configured to provide a predetermined level of electrical current and measure the voltage required to maintain the predetermined level of electrical current. Alternatively, each current detector 600 can be any electrical circuit that is configured to measure the blockage current of a combination of a graphene portion 20, a nanoscale hole therein, and atoms of a linear chain of a macromolecule to pass through the nanoscale hole. As used herein, macromolecules refer to macromolecules as known in biochemistry, which include nucleic acids, proteins, carbohydrates, and non-polymeric molecules with large molecular mass such as lipids and macrocycles.

The first electrode 410 and the second electrode 420, if present in the first chamber and the second chamber, respectively, at this step, can be electrically wired to form a portion of a gel electrophoresis circuit. The first electrode 410 can be connected to a variable voltage supply source 400 by a first insulated wire 412, and the second electrode 420 can be connected to the variable voltage supply source 400 by a second insulated wire 422. The first insulated wire 412 and the second insulated wire 422 can be routed through enclosure walls or through a sealed gap (e.g., between a container and a lid of the enclosure or between a sealing surface in a clamshell configuration).

The enclosure is subsequently filled with a sol, which is at a temperature above a sol/gel transition temperature. The filling of the enclosure with the sol can be performed, for example, by removing the first enclosure opening cap 212 and the second enclosure opening cap 222, and by injecting the sol 300 through the first enclosure opening 211 while letting a residual gas out of the enclosure 200 through the second enclosure opening 221. A gel 300 is subsequently formed in the enclosure 200 after the sol cools below the sol/gel transition temperature. The composition of the sol can be selected so that the gel 300 subsequently formed has a desired level of pore density and desired pore sizes therein. For example, the composition of the sol can be selected so that the gel 300 is conducive to gel electrophoresis of macromolecules to be transported and analyzed in the exemplary gel electrophoresis apparatus of the present disclosure. In other words, the pore size and concentration of the gel 300 may be optimized for gel electrophoresis of the macromolecules. In one embodiment, the composition of the sol can be selected so that the gel 300 is conducive to gel electrophoresis of single strand deoxyribonucleic acid (SSDNA).

If the first electrode 410 and/or the second electrode 420 are not installed in the enclosure before injection of the sol, the enclosure is opened and the first electrode 410 and the second electrode 420 are installed in the enclosure at this point. A buffer solvent may be optionally added around the first electrode 410 and/or around the second electrode 420. The buffer solvent may be the same solvent that is employed to form the sol. The buffer solvent may be inserted around the first electrode 410 and/or the around the second electrode 420 by opening the first and/or second enclosure opening caps (212, 222) and by inserting a tip of a pipette near the first electrode 410 and/or the second electrode 420. The buffer solvent can flow from the pipette into regions around the first electrode 410 and/or into regions around the second electrode 420. The buffer solvent functions as an ionic salt solution reservoir that prevents the gel 300 from drying.

Macromolecules 500 including a linear chain can be inserted into the first chamber, for example, by a pipette. The macromolecules 500 can be disposed between the first electrode 410 and the plate structure (100 or 100'). In one embodiment, the macromolecules can be SSDNA molecules, which are typically negatively charged.

Gel electrophoresis is performed to move the macromolecules 500 through the plate structure (100 or 100') toward the second electrode 420. The polarity of the voltage applied across the first electrode 410 and the second electrode 420 is selected to enable the movement of the macromolecules 500 away from the first electrode 410 and toward the second electrode 420. If the macromolecules 500 have positive electrical charges, a positive voltage is applied to the first electrode 410 and a negative voltage is applied to the second electrode 420. In this case, the first electrode 410 functions as an anode and the second electrode 420 functions as a cathode of the gel electrophoresis process. If the macromolecules 500 have negative electrical charges (as in the case of DNA strands), a negative voltage is applied to the first electrode 410 and a positive voltage is applied to the second electrode 420. In this case, the first electrode 410 functions as a cathode and the second electrode 420 functions as an anode of the gel electrophoresis process.

The macromolecules 500 are induced to pass through the divider plate, i.e., the plate structure (100 or 100'), by performing gel electrophoresis across the first chamber and the second chamber of the enclosure. The macromolecules 500 translocate through the portion of the gel 300 in the first chamber, through the plate structure (100 or 100'), and through the portion of the gel 300 in the second chamber. During the gel electrophoresis process, one of the macromolecules 500 is induced to pass through a nanoscale hole in one of the at least one graphene portion 20.

The magnitude of the electrical voltage applied across the first electrode 410 and the second electrode 420 is a function of the physical dimension between the first electrode 410 and the second electrode 420, of the property of the gel 300, and of the desired speed with which a linear chain in a macromolecule 500 passes through a nanoscale hole in one of the at least one graphene portion 20. In an illustrative example, if the physical distance between the first electrode 410 and the second electrode 420 is on the order of 1 cm, and if the target speed with which a linear chain of a macromolecule 500 passes through a nanoscale hole is about 0.2 nm/msec, the magnitude of the electrical voltage to be applied across the first electrode 410 and the second electrode 420 can be in a range from 2 V DC to 10 V DC, although properties of the gel 300 can cause this voltage to be greater than 10 V DC or to be less than 2 V DC.

The linear chain of a macromolecule 500 that passes through a funnel-shaped pore 11, a nanoscale hole through a graphene portion 20 and optionally through a dielectric material layer 30, and optionally through an additional funnel-shaped pore 11' is linearized at least at the nanoscale hole due to the geometry of the funnel-shaped pore 11 (and optionally due to the geometry of the additional funnel-shaped pore 11') and due to the smaller diameter of the nanoscale hole. Thus, the physical shape of the portion of the linear chain of the macromolecule 500 that passes through a nanoscale hole can be a substantially straight line, which is conducive to characterization of the sequence of component molecules of the linear chain. This feature is especially useful if the macromolecule 500 that passes through the nanoscale hole has a tendency to curl and/or fold over to form hairpin structures as in the case of SSDNA or double strand deoxyribonucleic acid (DSDNA). Thus, if an SSDNA molecule passes through the nanoscale hole, the physical shape of the portion of the SSDNA that passes through a nanoscale hole can be a substantially straight line, and as such, the portion of the SSDNA is conducive to characterization of the base sequence in the SSDNA.

Control of the speed of the translocation of the linear chain of the macromolecule 500 that passes through a nanoscale hole in the exemplary gel electrophoresis apparatus can be easily achieved by changing the magnitude of the electrical voltage across the first electrode 410 and the second electrode 420. The magnitude of the electrical voltage across the first electrode 410 and the second electrode 420 can be increased to increase the speed of translocation of the linear chain of the macromolecule 500, and can be decreased to decrease the speed of translocation of the linear chain of the macromolecule 500. In one embodiment, the speed of translocation of the linear chain of the macromolecule 500 can be in a range from 0.05 nm/msec to 0.5 nm/msec, although lesser and greater speeds can also be employed.

While ballistic transport phenomenon exists in each graphene portion 20, the characteristics of the ballistic transport is affected by the presence of the nanoscale hole and the atoms of the linear chain of the macromolecule 500 that passes through the nanoscale hole. Thus, the disturbance in electrical resistance of the graphene portion 20 induced by the macromolecule 500 that pass through the nanoscale hole can be measured employing the current detector 600 attached to the graphene portion 20. The change in the blockage current of the graphene portion 20 depends on the type of atoms that is present in the linear chain of the macromolecule 500 that passes the nanoscale hole. Thus, the types of atoms and/or the types of constituent molecules (such as individual bases on an SSDNA) can be characterized employing the exemplary gel electrophoresis apparatus of the present disclosure.

In case a plurality of graphene portions 20 are employed, the size of the nanoscale holes in the graphene portions 20 can be selected differently so that linear chains of macromolecules 500 with different lateral dimensions can be simultaneously analyzed, or linear chains of the same macromolecules 500 may be analyzed with different sensitivities. Thus, depending on the value of the third lateral dimension d3, which can be in a range from 1 nm to 10 nm, analysis of macromolecules 500 having different sizes of linear chains and/or analysis of macromolecules with different sensitivities are possible.

EXAMPLE

Translocation of DSDNA and SSDNA was demonstrated in 1% agarose gel in 0.1M-1 M KCl buffer in an experimental gel electrophoresis apparatus built according to the design of the exemplary gel electrophoresis apparatus illustrated in FIG. 7. The use of a sol/gel medium solves the serious problems associated with DNA interactions with hydrophilic or hydrophobic surfaces. The use of DC electric potential of 2-9 V allows one to electrophorese the DNA molecules with control speeds (velocity) across a test plate structure 100 at speeds on the order of 0.2 nm/msec. The "trapping" of these molecules in this gel system should allow the ratcheting of molecules through the detection device of the system, which includes a graphene portion 20 with a 2 nm nanoscale hole therein. Since the distance between base pairs is 0.5 nanometers the detector should have a thickness less than 0.5 nanometers. Such slow speed of translocation enabled quantitative measurement of the blockage current of a graphene portion 20 due to the passage of the SSDNA or DSDNA, which was previously impossible due to high speeds of translocation.

In this gel system, the pore size of the gel could be controlled by changing the concentration of the gel or using gels of smaller pore size or cross linking structures (acrylamide). A density gradient of pore size could also be employed. The use of density gradient gels is believed to have helped in the linearization of SSDNA for passage through the 200 nanometer and 20 nanometer pores and the detector. The gel was introduced into an enclosure including a plate structure 100 with a reservoir on both sides in the heated sol state. Then, the sol (agarose gel made up with buffer) was cooled and the material goes through a sol/gel transition. The translocation of both SSDNA and DSDNA through a plate structure 100 having a thickness of 53 microns with d1 of 200 nm, d2 of 20 nm, and d3 of 2 nm has been demonstrated.

It is noted that the system can also be configured with a combination of both gel and sol. Further, it is noted that the sol portions can be disposed on both sides of the plate structure 100 and around the first and second electrodes (410, 420) and act as a buffer reservoir and contact area for the first and second electrodes (410, 420).

While the disclosure has been described in terms of specific embodiments, it is evident in view of the foregoing description that numerous alternatives, modifications and variations will be apparent to those skilled in the art. Each of the various embodiments of the present disclosure can be implemented alone, or in combination with any other embodiments of the present disclosure unless expressly disclosed otherwise or otherwise impossible as would be known to one of ordinary skill in the art. Accordingly, the disclosure is intended to encompass all such alternatives, modifications and variations which fall within the scope and spirit of the disclosure and the following claims.

What is claimed is:

1. A method of operating an apparatus comprising:
providing an apparatus including an enclosure divided into a first chamber and a second chamber by a divider plate, said divider plate comprising a porous material layer comprising funnel-shaped pores between a first side surface and a second side surface, wherein said first side surface is a peripheral surface of said first chamber and said second side surface is a peripheral surface of said second chamber, and each of said funnel-shaped pores has a smaller opening at said first side surface than an opening at said second side surface and wherein each funnel-shaped pore has at least one tapered portion in which a cross sectional area decreases with distance from a geometrical center of each funnel-shaped pore, said divider plate further comprising a graphene portion directly contacting said first side surface, wherein a nanoscale hole extends through said graphene portion and to one of said funnel-shaped pores and is in direct communication with said smaller opening of one of said funnel-shaped pore;
filling said enclosure with a sol having a sol/gel transition temperature;
converting said sol into a gel by cooling said sol below said sol/gel transition temperature;
inserting macromolecules including a linear chain into said first chamber; and
inducing said macromolecules to pass through said divider plate by performing gel electrophoresis across said first chamber and said second chamber.

2. The method of claim 1, wherein said divider plate further comprises a coating of a dielectric material layer located on a surface of said graphene portion and portions of said first side surface that are not in contact with said graphene portion.

3. The method of claim 1, wherein said method further comprises inducing one of said macromolecules to pass through said nanoscale hole.

4. The method of claim 3, further comprising measuring a blockage current of said graphene portion induced by said one of said macromolecules that pass through said nanoscale hole.

5. The method of claim 4, wherein said divider plate further comprises a pair of contact structures in physical contact with two regions of said graphene portion and a pair of conductive lead wires in contact with said pair of contact structures, and said blockage current is measured by measuring a change in electrical current between said pair of contact structures.

6. The method of claim 1, wherein said porous material layer comprises aluminum oxide, and said funnel-shaped pores have a lateral dimension in a range from 50 nm to 800 nm at said second side surface, and have a lateral dimension in a range from 4 nm to 50 nm at said first side surface.

7. The method of claim 1, wherein said filling said enclosure with said sol is by injection of a sol composition.

* * * * *